US008664446B1

(12) United States Patent
Besancon et al.

(10) Patent No.: US 8,664,446 B1
(45) Date of Patent: Mar. 4, 2014

(54) PURIFICATION OF TRIMETHYLAMINE

(71) Applicant: American Air Liquide, Inc., Fremont, CA (US)

(72) Inventors: Brian Besancon, Lincoln University, PA (US); Christian Dussarrat, Toyko (JP); Nathan Stafford, Damascus, OR (US); Paul Jantzen, Ballston Spa, NY (US)

(73) Assignee: American Air Liquide, Inc., Fremont, CA (US)

( * ) Notice: Subject to any disclaimer, the term of this patent is extended or adjusted under 35 U.S.C. 154(b) by 0 days.

(21) Appl. No.: 13/731,297

(22) Filed: Dec. 31, 2012

(51) Int. Cl.
*C07C 209/84* (2006.01)
*C07C 209/86* (2006.01)

(52) U.S. Cl.
USPC ............................... 564/497; 564/499

(58) Field of Classification Search
None
See application file for complete search history.

(56) References Cited

PUBLICATIONS

Database CAPLUS on STN, Acc. No. 2002:955412, Hoshino et al., JP 2002363140 A, Dec. 18, 2002 (abstract).*
Armarego, W.L.F. et al., "Purification of Laboratory Chemicals," 2009, 6$^{th}$ ed., p. 190.
Sigma-Aldrich Product No. 243205 specification sheet downloaded from http://www.sigmaaldrich.com/catalog/product/aldrich/243205?lang=en&region=US; accessed on Sep. 13, 2012, 1 pg.

* cited by examiner

*Primary Examiner* — Brian J Davis
(74) *Attorney, Agent, or Firm* — Patricia E. McQueeney

(57) ABSTRACT

Methods of purifying $NMe_3$ by removing $N_2$, $NH_2Me$, $NH_3$, and $H_2O$ are disclosed.

18 Claims, 2 Drawing Sheets

PURIFICATION OF TRIMETHYLAMINE

BACKGROUND

Trimethylamine ($NMe_3$) is commercially available at purity levels of approximately 99.0 area % (by gas chromatography). See, e.g. Sigma-Aldrich Product Nos. 243205. Applications in the electronics, semiconductor, and photovoltaic industries require higher purity trimethylamine. Impurities present in trimethylamine may include nitrogen ($N_2$), ammonia ($NH_3$), monomethylamine ($NH_2Me$), dimethylamine ($NHMe_2$), water ($H_2O$), and methanol (MeOH). Amarego et al. disclose a couple of methods that may be used to further purify trimethylamine, including using freshly sublimed and ground $P_2O_5$ to remove water and impurities containing labile hydrogen (Purification of Laboratory Chemicals, 2009, page 190). The disclosed processes are complex, time consuming and employ the use of materials that are difficult to handle.

A need remains for an efficient method to remove $N_2$, $H_2O$, $NH_3$, and $NH_2Me$ from available $NMe_3$ supplies.

SUMMARY

Disclosed are methods of purifying a trimethylamine-containing gas. The amount of monomethylamine in the trimethylamine-containing gas is reduced below 5 ppm by area by passing the trimethylamine-containing gas through a zeolite 5 A molecular sieve. The disclosed methods may include one or more of the following aspects:
- the purified trimethylamine-containing gas containing less than 1 ppm by area monomethylamine;
- reducing an amount of $N_2$ in the trimethylamine-containing gas below 10 ppm by area by separating $N_2$ from the trimethylamine-containing gas;
- separating $N_2$ from the trimethylamine-containing gas by heating and cooling a container of the trimethylamine-containing gas while simultaneously venting $N_2$ from the container;
- separating $N_2$ from the trimethylamine-containing gas by distillation;
- the purified trimethylamine-containing gas containing less than 5 ppm by area $N_2$;
- reducing an amount of $H_2O$ and $NH_3$ in the trimethylamine-containing gas by passing the trimethylamine-containing gas through a 3 A or 4 A molecular sieve;
- the purified trimethylamine-containing gas containing less than 5 ppm by area $H_2O$ and less than 5 ppm by area $NH_3$;
- receiving the purified trimethylamine-containing gas in a cylinder cooled to a temperature ranging from approximately −10° C. to approximately 5° C.; and
- the purified trimethylamine-containing gas being 99.99 area trimethylamine.

Also disclosed are purification methods for $NMe_3$. $NMe_3$ is passed through a zeolite 5 A molecular sieve and $N_2$ is separated from $NMe_3$ to produce purified $NMe_3$. The disclosed methods may have one or more of the following aspects:
- the purified $NMe_3$ containing less than 10 ppm by area $N_2$ and less than 5 ppm by area $MeNH_2$;
- the purified $NMe_3$ containing less than 5 ppm by area $N_2$;
- passing $NMe_3$ through a 3 A or 4 A molecular sieve;
- the purified $NMe_3$ containing less than 5 ppm by area $H_2O$;
- the purified $NMe_3$ containing less than 5 ppm by area $NH_3$.
- receiving the purified $NMe_3$ in a cylinder cooled to a temperature ranging from approximately −10° C. to approximately 5° C.; and
- the purified $NMe_3$ being 99.99 area % trimethylamine.

NOTATION AND NOMENCLATURE

Certain abbreviations, symbols, and terms are used throughout the following description and claims and include:

The standard abbreviations of the elements from the periodic table of elements are used herein. It should be understood that elements may be referred to by these abbreviations (e.g., Si refers to silicon, Hf refers to hafnium, Zr refers to zirconium, Pd refers to palladium, Co refers to cobalt, etc).

The percentages calculated herein were calculated based on the area displayed in the gas chromatograms compared to the peak area of a calibrated standard and are referred to as "area %" or "ppm by area".

BRIEF DESCRIPTION OF THE FIGURES

For a further understanding of the nature and objects of the present invention, reference should be made to the following detailed description, taken in conjunction with the accompanying figure wherein.

DETAILED DESCRIPTION OF PREFERRED EMBODIMENTS

Methods of purifying trimethylamine-containing gases, including "pure" trimethylamine gas, are disclosed. The trimethylamine purified by the disclosed methods may contain between approximately 99.99 area % (4 9s or 4N) and approximately 99.999 area % (5 9s or 5N) trimethylamine.

Due to the reactivity of $NMe_3$ and $NMe_3$-containing gases, the disclosed purification methods and any subsequent storage should be performed in systems and stored in vessels through which inert gas previously flowed to remove air and moisture. Exemplary inert gases include $N_2$, Ar, He, and combinations thereof. In the following examples, He was used. When $N_2$ is used, any residual amounts of $N_2$ remaining in the system will be removed from the $NMe_3$ during the purification. The stainless steel components of the purification system should undergo complete electro polish and drying.

In order to prevent generation of additional impurities in the purified $NMe_3$ gas, it should be stored in cylinders having surfaces with which the $NMe_3$ does not react. Suitable surfaces include steel, carbon steel with Ni coating, aluminum, stainless steel, glass, quartz, nylon, metal alloys sold under the trademark Monel®, metal alloys sold under the trademark Hastelloy®, fluorine-containing resins sold under the trademark Teflon®, synthetic rubber sold under the trademark Kalrez®, and/or glassware sold under the trademark Pyrex®. Preferably, the purified $NMe_3$ is stored in cylinders made of aluminum or carbon steel with Ni coating. Please note that amines are incompatible with many common o-ring and seal materials, such as synthetic rubber sold under the trademark Viton®.

$NMe_3$-containing gas is commercially available. $NMe_3$ is most often produced by distillation of a gas stream containing dimethylamine, monomethylamine, ammonia, methanol, and water. The distillation produces a $NMe_3$-containing gas comprising approximately 99 area % $NMe_3$.

Commercially available NMe₃-containing gas contains between approximately 500 ppm by area and approximately 5 area % $N_2$ and between approximately 500 ppm by area and approximately 0.5 area % monomethylamine. Other impurities may include water ($H_2O$), ammonia ($NH_3$), and dimethylamine ($NHMe_2$).

Monomethylamine and/or $H_2O$ quantities in the NMe₃-containing gas may be reduced by flowing the NMe₃-containing gas through a zeolite 5 A molecular sieve. The presence of moisture may contribute to the corrosion of piping and gas distribution systems even at very low concentrations. The NMe₃-containing gas contacts the zeolite 5 A molecular sieve by flowing through a container of the zeolite 5 A molecular sieve. The zeolite 5 A molecular sieve is commercially available. Currently, zeolite 5 A molecular sieve is supplied as 1.7-2.5 mm or 3-5 mm beads or 1.6 mm or 3.2 mm pellets. Any of these sizes may be used in the disclosed methods.

Figure 1A:
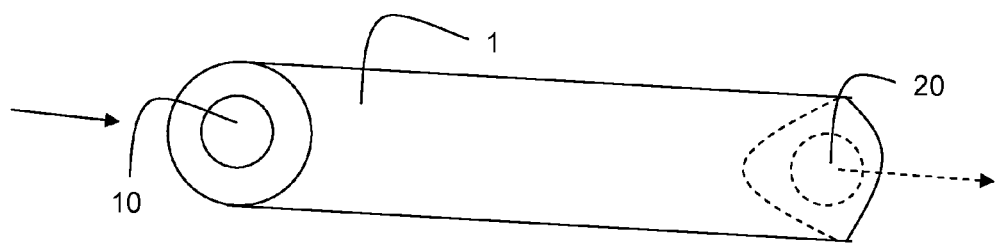
FIG. 1a is an illustration of an exemplary purification container.

The zeolite 5 A molecular sieve may be placed in a container made of stainless steel. Alternatively, the zeolite 5 A molecular sieve may be placed in a container made of aluminum, stainless steel passivated by $SiH_4$, or nickel plated carbon steel. The container should have an inlet and outlet. In one alternative, depicted in FIG. 1A, the inlet 10 and outlet 20 are located on opposite ends of the container 1 in order to minimize dead flow zones within the molecular sieve. The arrows in FIG. 1A depict the direction of gas flow through the container 1. However, alternative inlet and outlet locations may also be desired, such as the inlet 10 being located on one end of a cylindrical container 1 with the outlet 20 located on the cylindrical surface of the container 1 at the other end of the container 1. One of ordinary skill in the art will recognize that the shape of the container 1 is not limited to a cylinder, but may also include spherical, cubic, or other polyhedric shapes.

The commercially available zeolite 5 A molecular sieve is provided in its activated state by the manufacturer. Applicants, however, re-activate the zeolite 5 A molecular sieve prior to use in order to remove any contaminants that may have been adsorbed during transport from the manufacturer, during transport from its original container to the purification container, or from the purification container itself. Applicants activate the zeolite 5 A molecular sieve by heating it to a temperature ranging from approximately 150° C. to approximately 250° C. under an inert gas for approximately 10 to approximately 24 hours. The inert gas may be $N_2$, Ar, He, or combinations thereof. One of ordinary skill in the art will recognize that the amount of molecular sieve to be activated will determine the activation time and temperature, with larger quantities requiring either longer times or higher temperatures and smaller quantities requiring less time or lower temperatures. The zeolite 5 A may be activated by heating to temperatures as high as 600° C. However, heating the zeolite 5 A to such temperatures will require the remaining components in the purification system, such as valves, to become more expensive because they will be engineered to withstand exposure to such temperatures. As a result, activation at temperatures below 300° C. permits the use of less expensive valves in the purification system.

In order to reduce the amount of $NH_2Me$ and/or $H_2O$ in the NMe₃-containing gas, the NMe₃-containing gas flows through the zeolite 5 A molecular sieve that has been prepared in accordance with the paragraph above. The NMe₃-containing gas should remain in contact with the zeolite 5 A molecular sieve for approximately 0.5 seconds to approximately 100 seconds, and preferably from approximately 2 seconds to approximately 40 seconds. The process may take place at room temperature (approximately 15° C. to approximately 30° C.). Alternatively, the process may take place at a temperature ranging from approximately 0° C. to approximately 35° C.

The resulting NMe₃-containing gas contains less than 5 ppm by area $NH_2Me$, and preferably less than 1 ppm by area $NH_2Me$, and contains between approximately 95 area % and approximately 99.95 area % NMe₃. As will be described in further detail below, the order of removal of the impurities is not critical. Therefore, if $N_2$ is removed from the NMe₃-containing gas first by the methods described in further detail below, the resulting NMe₃-containing gas contains between approximately 99.995 area % and approximately 99.999 area % NMe₃ after removal of the $NH_2Me$.

Water ($H_2O$) and/or ammonia ($NH_3$) quantities in the NMe₃-containing gas may also be reduced by flowing the NMe₃-containing gas through 3 A or 4 A molecular sieve. The 3 A and 4 A molecular sieves are commercially available. Currently, 3 A molecular sieve is supplied as 4×8 beads, 8×12 beads, ¹⁄₁₆" pellets and ⅛" pellets. Currently, 4 A molecular sieve is supplied as 14×30 granular, 10×20 beads, 8×12 beads, 4×8 beads, ¹⁄₁₆" pellets, and ⅛" pellets. Any of these sizes may be used in the disclosed methods.

Figure 1B:
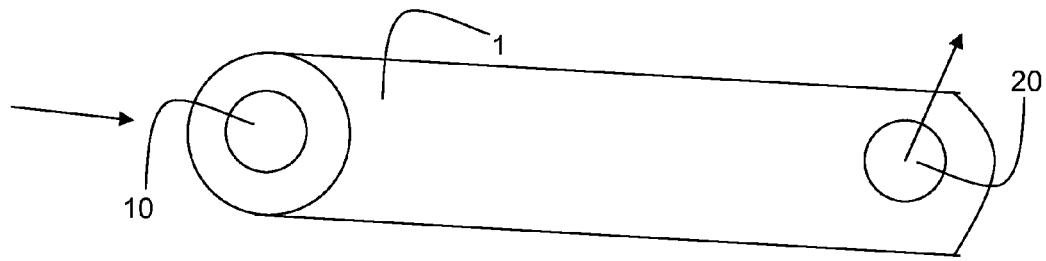
FIG. 1b is an illustration of an alternate purification container.

Like the zeolite 5 A molecular sieve, the 3 A or 4 A molecular sieve may be stored in a stainless steel container. Alternatively, the 3 A or 4 A molecular sieve may be placed in a container made of aluminum, stainless steel passivated with $SiH_4$, or nickel plated carbon steel. Like the container for the zeolite 5 A molecular sieve, the container for the 3 A or 4 A molecular sieve should have an inlet and outlet. In one alternative, depicted in FIG. 1A, the inlet 10 and outlet 20 are located on opposite ends of the container 1 in order to minimize dead flow zones within the molecular sieve. The arrows in FIG. 1A depict the direction of gas flow through the container 1. However, alternative inlet and outlet locations may also be desired, such as the inlet 10 being located on one end of a cylindrical container 1 with the outlet 20 located on the cylindrical surface of the container 1 at the other end of the container 1 as depicted in FIG. 1B. One of ordinary skill in the art will recognize that the shape of the container 1 is not limited to a cylinder, but may also include spherical, cubic, or other polyhedric shapes.

Prior to use, the 3 A or 4 A molecular sieve is activated by heating it under an inert gas to a temperature ranging from approximately 150° C. to approximately 250° C. for approximately 10 to approximately 24 hours. The inert gas may be $N_2$, Ar, He, or combinations thereof. $N_2$ is adsorbed on the 4 A molecular sieve at these temperatures. Therefore, a He purge should follow activation of the 4 A molecular sieve under a $N_2$ atmosphere in order to produce a purified NMe₃ gas having low quantities of $N_2$. For each 500 g of 4 A molecular sieve, the flow of the inert gas should be proportional to approximately 100 cc/min (i.e. 500 g=100 cc/min; 1 kg=200 cc/min, etc.). After approximately 8 hours of He purge, purification of the NMe₃-containing gas may begin. One of ordinary skill in the art will recognize that different amounts of 4 A may require a longer or shorter activation period.

In order to reduce the amount of $H_2O$ and/or $NH_3$ in the NMe₃-containing gas, the NMe₃-containing gas is passed through the 3 A or 4 A molecular sieve that has been prepared in accordance with the paragraph above. The NMe₃-containing gas should remain in contact with the 4 A molecular sieve for approximately 0.5 seconds to approximately 100 seconds, and preferably from approximately 2 seconds to approximately 40 seconds. The process may take place at room temperature (approximately 15° C. to approximately 30° C.). Alternatively, the process may take place at a temperature ranging from approximately 0° C. to approximately 35° C. The resulting $NMe_3$-containing gas has less than 5 ppm by area each of $H_2O$ and $NH_3$, and preferably less than 1 ppm by area each of $H_2O$ and $NH_3$, and contains 95.5 area % and approximately 99.99 area % $NMe_3$. As will be described in further detail below, the order of removal of the impurities is not critical. Therefore, if $N_2$ is removed from the $NMe_3$-containing gas first by the methods described in further detail below, the resulting $NMe_3$-containing gas contains between approximately 99.995 area % and approximately 99.999 area % $NMe_3$ after removal of the $NH_2Me$, $H_2O$, and $NH_3$.

The water and/or ammonia reduction step using the 3 A or 4 A molecular sieve may occur before or after the $NH_2Me$ and/or $H_2O$ reduction step using the zeolite 5 A molecular sieve. In another alternative, both the zeolite 5 A molecular sieve and the 3 A or 4 A molecular sieve may be stored in the same container to simultaneously reduce the quantities of $H_2O$, $NH_3$, and $NH_2Me$.

To separate $N_2$ from $NMe_3$, the $NMe_3$-containing gas may be cooled to a temperature ranging from approximately −10° C. to approximately 5° C. Alternatively, after removing $NH_2Me$, $H_2O$, and/or $NH_3$, the $NMe_3$-containing gas may be transferred to one or more cylinders having a temperature ranging from approximately −10° C. to approximately 5° C. The cylinder(s) may be located on a scale to assure that the cylinder(s) is not overfilled with $NMe_3$. $N_2$ may be vented from the cooled cylinder(s). To reduce loss of $NMe_3$ during $N_2$ venting, the cylinder(s) may be heated to a temperature ranging from approximately 30° C. to approximately 40° C. and then cooled again to a temperature ranging from approximately −10° C. to approximately 5° C. This heating/cooling process may be repeated several times. The heating/cooling cycle during venting provides a significant reduction in product loss compared to venting the cooled cylinder(s) without the heating/cooling cycle. However, care should be taken to prevent cooling the cylinder(s) to too low a temperature. When experiments were performed using dry ice to cool the cylinder(s), the TMA was cooled too much (the boiling point of TMA is 4° C. and dry ice cools to approximately −78° C.), which prevented removal of $N_2$ in a quick manner. Furthermore, some of the $N_2$ may have been soluble in the cold TMA because the $N_2$ concentration rose by several hundred ppm after the cylinder(s) was allowed to warm overnight. As a result, an ice bath or heating jacket cooled to a temperature ranging from approximately −10° C. to approximately 5° C. is optimum for $N_2$ removal.

Alternatively, to separate $N_2$ from larger quantities of $NMe_3$-containing gas, the $NMe_3$-containing gas may be transferred from the molecular sieves to a vessel or boiler suitable for distillation.

$N_2$ may be separated from $NMe_3$ before or after reducing the quantities of $NH_2Me$, $H_2O$, and/or $NH_3$ in the $NMe_3$-containing gas. As the zeolites may contain residual $N_2$ from the activation process, $N_2$ separation preferably occurs after reduction of $NH_2Me$, $H_2O$, and/or $NH_3$.

Figure 2:
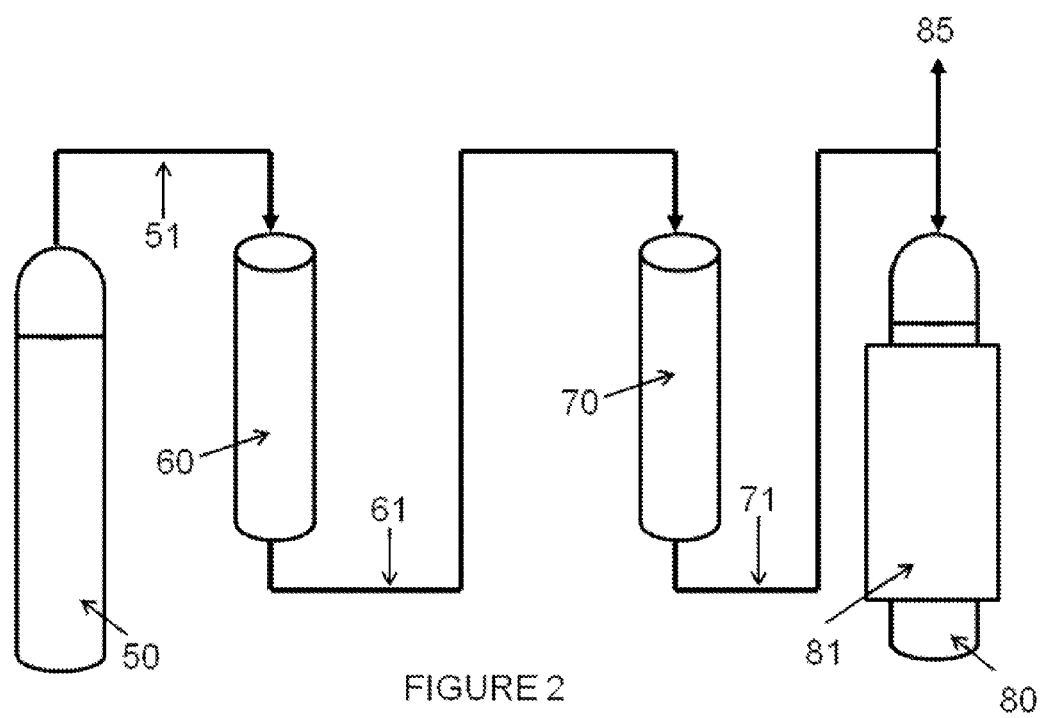
FIG. 2 is an illustration of an exemplary purification system.

One exemplary purification system is depicted in FIG. 2. The $NMe_3$-containing gas is contained in the cylinder 50. The cylinder valve (not shown) is opened allowing the $NMe_3$-containing gas to flow through valves and piping 51 into Vessel 60 containing one of the disclosed molecular sieves in order to remove $H_2O$ and $NH_3$ and/or $H_2O$ and $NH_2Me$ from the $NMe_3$-containing gas. A valve, not shown, in valves and piping 61 is opened to allow the $NMe_3$-containing gas to flow to Vessel 70 containing a different molecular sieve than contained in Vessel 60. For example, if Vessel 60 contains zeolite 5 A, Vessel 70 contains 3 A or 4 A. Alternatively if Vessel 60 contains 3 A or 4 A, Vessel 70 contains zeolite 5 A. In another alternative, both Vessel 60 and Vessel 70 may contain both zeolite 5 A and 3 A or 4 A. The purified $NMe_3$ then flows through valves and piping 71 into cylinder 80 (when the cylinder valve, not shown, is open). A heating/cooling jacket 81 may be used to heat and cool the cylinder 80 to reduce the quantities of $N_2$ in the TMA via vent 85.

One of ordinary skill in the art will recognize the sources for the components of the systems used to practice the disclosed methods. Some level of customization of the components may be required based upon the desired temperature range, pressure range, local regulations, etc. Exemplary suppliers include Büchi Glas Uster AG, Shandong ChemSta Machinery Manufacturing Co. Ltd., Jiangsu Shajabang Chemical Equipment Co. Ltd, etc. Preferably the components are made of corrosion resistant materials, such as glass lined steel, steel with corrosion resistant liners, etc.

EXAMPLES

The following non-limiting examples are provided to further illustrate embodiments of the invention. However, the examples are not intended to be all inclusive and are not intended to limit the scope of the inventions described herein.

Example 1

Two separate chromatography columns were used to determine detection capabilities. Both columns claimed the ability to detect air, water, MMA, DMA, TMA, and ethylene diamine. The first column, a HaySep B column, only demonstrated the ability to detect $N_2$, MMA, TMA, and MeOH. The second column, a RTX amine column, only demonstrated the ability to detect MMA, DMA, and TMA.

Example 2

Analysis of commercially available trimethylamine was performed using gas chromatography and the HaySep B column. The initial product contained approximately 4 area % $N_2$ and approximately 0.24 area % monomethylamine. $NH_3$, methanol, and dimethylamine were not detected. The $N_2$ quantity was reduced to 2.3 ppm by area by venting, but approximately 15% of the TMA was also vented. The monomethylamine quantity was reduced to 8 ppm by area using a 5 A molecular sieve. The resulting product was 99.999 area % TMA.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

The invention claimed is:

1. A method of purifying a trimethylamine-containing gas, the method comprising reducing an amount of monomethylamine in the trimethylamine-containing gas below 5 ppm by area by passing the trimethylamine-containing gas through a zeolite 5 A molecular sieve.

2. The method of claim 1, wherein the purified trimethylamine-containing gas contains less than 1 ppm by area monomethylamine.

3. The method of claim 1, further comprising reducing an amount of $N_2$ in the trimethylamine-containing gas below 10 ppm by area by separating $N_2$ from the trimethylamine-containing gas.

4. The method of claim 3, wherein $N_2$ is separated from the trimethylamine-containing gas by heating and cooling a container of the trimethylamine-containing gas while simultaneously venting $N_2$ from the container.

5. The method of claim 3, wherein $N_2$ is separated from the trimethylamine-containing gas by distillation.

6. The method of claim 3, wherein the purified trimethylamine-containing gas contains less than 5 ppm by area $N_2$.

7. The method of claim 1, further comprising reducing an amount of $H_2O$ and $NH_3$ in the trimethylamine-containing gas by passing the trimethylamine-containing gas through a 3 A or 4 A molecular sieve.

8. The method of claim 7, wherein the purified trimethylamine-containing gas contains less than 5 ppm by area $H_2O$ and less than 5 ppm by area $NH_3$.

9. The method of claim 1, further comprising receiving the purified trimethylamine-containing gas in a cylinder cooled to a temperature ranging from approximately −10° C. to approximately 5° C.

10. The method of claim 9, wherein the purified trimethylamine-containing gas is 99.99 area % trimethylamine.

11. A purification method for $NMe_3$, the method comprising:
passing $NMe_3$ through a zeolite 5 A molecular sieve; and
separating $N_2$ from $NMe_3$ to produce purified $NMe_3$.

12. The method of claim 11, wherein the purified $NMe_3$ contains less than 10 ppm by area $N_2$ and less than 5 ppm by area $MeNH_2$.

13. The method of claim 12, wherein the purified $NMe_3$ contains less than 5 ppm by area $N_2$.

14. The method of claim 11, further comprising passing $NMe_3$ through a 3 A or 4 A molecular sieve.

15. The method of claim 14, wherein the purified $NMe_3$ contains less than 5 ppm by area $H_2O$.

16. The method of claim 14, wherein the purified $NMe_3$ contains less than 5 ppm by area $NH_3$.

17. The method of claim 11, further comprising receiving the purified $NMe_3$ in a cylinder cooled to a temperature ranging from approximately −10° C. to approximately 5° C.

18. The method of claim 11, wherein the purified $NMe_3$ is 99.99 area % trimethylamine.

* * * * *